(12) United States Patent
Dornish et al.

(10) Patent No.: US 8,257,727 B2
(45) Date of Patent: Sep. 4, 2012

(54) MEDICAL DEVICES COATED WITH A FAST DISSOLVING BIOCOMPATIBLE COATING

(75) Inventors: Michael Dornish, Bekkestua (NO); Christian Klein Larsen, Eiksmarka (NO); Therese Andersen, Sande i Vestfold (NO)

(73) Assignee: FMC Biopolymer AS, Sandvika (NO)

( * ) Notice: Subject to any disclaimer, the term of this patent is extended or adjusted under 35 U.S.C. 154(b) by 1748 days.

(21) Appl. No.: 11/486,836

(22) Filed: Jul. 14, 2006

(65) Prior Publication Data

US 2007/0077271 A1    Apr. 5, 2007

Related U.S. Application Data

(60) Provisional application No. 60/706,396, filed on Jul. 21, 2005.

(51) Int. Cl.
*A61F 2/00* (2006.01)
(52) U.S. Cl. ......................................... 424/423
(58) Field of Classification Search ................... None
See application file for complete search history.

(56) References Cited

U.S. PATENT DOCUMENTS

| | | | |
|---|---|---|---|
| 4,326,532 A | 4/1982 | Hammar et al. | |
| 4,487,865 A | 12/1984 | Balazs et al. | |
| 4,491,660 A * | 1/1985 | Gendrich et al. | 536/32 |
| 4,500,676 A | 2/1985 | Balazs et al. | |
| 5,688,855 A | 11/1997 | Stoy et al. | |
| 5,830,883 A | 11/1998 | Block et al. | |
| 5,900,408 A | 5/1999 | Block et al. | |
| 6,106,889 A | 8/2000 | Beavers et al. | |
| 6,129,956 A | 10/2000 | Morra et al. | |
| 6,150,581 A * | 11/2000 | Jiang et al. | 602/50 |
| 6,160,032 A | 12/2000 | Shah et al. | |
| 6,200,595 B1 * | 3/2001 | Motoyashiki et al. | 424/445 |
| 6,309,380 B1 | 10/2001 | Larson et al. | |
| 6,387,450 B1 | 5/2002 | Shah et al. | |
| 6,511,507 B2 | 1/2003 | Shah et al. | |
| 6,706,690 B2 * | 3/2004 | Reich et al. | 514/21 |
| 6,723,350 B2 * | 4/2004 | Burrell et al. | 424/618 |
| 2002/0115985 A1 * | 8/2002 | Larson et al. | 604/890.1 |
| 2002/0138025 A1 * | 9/2002 | Gellman et al. | 602/4 |
| 2003/0134132 A1 * | 7/2003 | Winterton et al. | 428/451 |
| 2003/0161938 A1 | 8/2003 | Johnson | |
| 2003/0208281 A1 | 11/2003 | Goldberg et al. | |
| 2004/0057978 A1 | 3/2004 | Mattes et al. | |
| 2004/0098119 A1 * | 5/2004 | Wang | 623/1.42 |
| 2004/0106987 A1 | 6/2004 | Palasis et al. | |
| 2004/0172048 A1 | 9/2004 | Browning | |
| 2006/0073184 A1 | 4/2006 | Xia et al. | |
| 2006/0127439 A1 | 6/2006 | Mattes et al. | |
| 2006/0198869 A1 | 9/2006 | Furst et al. | |
| 2006/0224038 A1 | 10/2006 | Rao et al. | |
| 2007/0059473 A1 | 3/2007 | Yamazaki et al. | |

FOREIGN PATENT DOCUMENTS

| | | |
|---|---|---|
| CA | 1300538 | 5/1992 |
| RU | 2240839 | 11/2004 |
| WO | WO-95/24168 A1 | 9/1995 |
| WO | WO-9733552 A1 | 9/1997 |
| WO | WO-02078568 A1 | 10/2002 |
| WO | WO-02092143 A1 | 11/2002 |
| WO | WO-03/092754 A1 | 11/2003 |
| WO | WO-2004028583 A2 | 4/2004 |
| WO | WO-2004/069230 A1 | 8/2004 |
| WO | WO-2004112863 A1 | 12/2004 |
| WO | WO-2005104845 A1 | 11/2005 |

OTHER PUBLICATIONS

NovaMatrix Product INformation Bulletin for Ultrapure and sterile PRONOVA TM sodium alginates, 2002.*
Efentakis and Koutlis, Pharm Dev Tech 6(1), p. 91-98, 2001.*
Notification of Transmittal of the International Search Report and the Written Opinion of the International Searching Authority, or the Declaration—Date of Mailing—Feb. 6, 2008—International Filing Date—Jul. 14, 2006.
Extended European Search Report dated Feb. 10, 2011.

* cited by examiner

*Primary Examiner* — Nissa Westerberg
(74) *Attorney, Agent, or Firm* — FMC Corporation

(57) ABSTRACT

The present invention relates to a medical device comprising a biocompatible medical coating adhered thereto, wherein the coating comprises at least one of a non-crosslinked, water soluble salt of: (i) alginic acid, (ii) hyaluronic acid or (iii) chitosan, wherein the coating is readily dissolvable in at least one mammalian body fluid.

26 Claims, No Drawings

MEDICAL DEVICES COATED WITH A FAST DISSOLVING BIOCOMPATIBLE COATING

RELATED APPLICATIONS

This application claims the benefit of U.S. Ser. No. 60/706,396, filed on Jul. 21, 2005.

FIELD OF THE INVENTION

The present invention relates to medical devices comprising a biocompatible medical coating adhered thereto, wherein the biocompatible medical coating comprises at least one of a non-crosslinked, water soluble salt of: (i) alginic acid, (ii) hyaluronic acid or (iii) chitosan, wherein the coating is readily dissolvable in at least one mammalian body fluid.

BACKGROUND OF THE INVENTION

It is known in the prior art that biopolymers such as alginate, chitosan and hyaluronan can be used to coat medical devices for topical use, such as wound dressings or for implantation on medical devices such as stents or catheters and as tissue or as biological encapsulants. Such coatings are designed to stay attached to the medical device or other substrate for desired periods of time or for the useful life of the medical device. In the prior art, the biopolymer component is typically cross-linked using divalent ions or chemical agents. The cross-linking agent may be contained in the coating formulation when the coating is applied to the substrate or provided in another step in the coating process. The cross-linked biopolymer coating can be hydrated to form a hydrogel that may dissolve over an extended period of time in contact with physiological fluids or other aqueous environment.

US 2004/0057978 discloses a medical device in a medical assembly for long term implantation in which an inorganic surface of a medical device is modified to form an adhesion promoting surface which is coated with an alginate solution and reacted with a cross-linking alkaline earth cation to form a gelled alginate coating.

WO 03092754 discloses ionically cross-linked alginate hydrogels that form self-supporting sheet or non-sheet forms and may partially or completely encapsulate a porous substrate such as a surgical mesh. The disintegration of the cross-linked biopolymer film is stated to encourage tissue growth into the mesh. The film exhibits a disintegration time measured at room temperature in saline up to about 72 hours.

US 2004/0172048 describes a surgical implant mesh material that preferably is at least partially encapsulated by an absorbable coating to improve its handling characteristics. The coating, covering or layer may be based on gelatin, starch, cellulose, alginate or hyaluronic acid and is preferably absorbed by the body within 48 hours following implantation such that it does not contribute to the foreign body mass retained in the body.

Despite the above prior art, there are occasions where there is a desirability that the coating dissolves after a short period of time exposing the surface of the medical device.

SUMMARY OF THE INVENTION

The present invention relates to medical devices comprising a biocompatible medical coating adhered thereto, wherein the coating comprises at least one of a non-crosslinked, water soluble salt of: (i) alginic acid, (ii) hyaluronic acid or (iii) chitosan, wherein the coating is readily dissolvable in at least one mammalian body fluid.

The present invention provides a coating on a medical device, instrument or structures which temporarily provides at least one of a protecting property, a lubricating property, a bioadhesive property to an instrument, or medical device.

DETAILED DESCRIPTION OF THE INVENTION

Soluble coatings for use in instruments and medical device applications are the coatings of the present invention that are water soluble and provide properties such as a lubricating property, increased lubricity; a protective property to mask or cover jagged, uneven, or sharp areas of the device; a bioadhesive property allowing the device to adhere to mucosal surfaces, tissues and organs. The biopolymer coating of the invention may also increase the ease of insertion, placement, movement or positioning of the device. Dissolution of the coating of the invention will then allow the permanent placement, anchoring or securement of the device.

The phrase "readily dissolvable" as used herein refers to biocompatible coatings of the invention that are fully dissolved in at least one mammal, e.g., human, bodily fluid generally within less than 3 hours, less than 2.5 hours, less than 2.0 hours, less than 1.5 hours, less than 1.0 hours, less than 50 minutes, less than 40 minutes and less than 30 minutes. The bodily fluids include blood serum, plasma, interstitial fluid, urine, gastric fluid, as desired. Examples of representative model body fluids that may be used to determine the dissolvability of coatings within the scope of this invention include 0.9% NaCl solution, Hanks' balanced salt solution or simulated gastric fluid.

Alginates are a family of non-branched binary copolymers of 1→4 glycosidically linked β-D-mannuronic acid (M) and α-L-guluronic acid (G) monomers. The relative amount of the two uronic acid monomers and their sequential arrangement along the polymer chain vary widely, depending on the origin of the alginate. The uronic acid residues are distributed along the polymer chain in a pattern of blocks, where homopolymeric blocks of G residues (G-blocks), homopolymeric blocks of M residues (M-blocks) and blocks with alternating sequence of M and G units (MG-blocks) co-exist. The alginate molecule cannot be described by the monomer composition alone. Composition and sequential structure together with molecular weight and molecular conformation are the key characteristics of alginate in determining its properties and functionality. The salts of alginic acid used in the present invention are non-crosslinked and water soluble.

Water soluble alginates suited for use in the present invention include both non crosslinked guluronic acid rich and mannuronic acid rich salts of alginic acid. The preferred alginic acid salt is sodium alginate, but potassium and magnesium alginate can also be used.

Pharmacokinetic studies of alginate have been carried out following administration of a [$^{14}$C] radiolabeled alginate purified from *Pseudomonas aeruginosa* (Skaugrud, Ø. et al., Biomedical and pharmaceutical applications of alginate and chitosan, *Biotech. Genetic Eng. Rev.*, 16, 23-40, 1999). The pharmacokinetics in mice following an intravenous (IV) bolus injection of 100 μg [$^{14}$C] alginate indicates a 2-compartment model. The data show an initial rapid elimination of alginate from the blood (0 to 5 hours) followed by a slower elimination (5-48 hours). The initial half-life ($t_{1/2}\alpha$) is approximately 4 hours, while the secondary half-life ($t_{1/2}\beta$) appears to be about 22 hours.

Preferred alginates are reduced endotoxin, well-characterized non crosslinked water soluble salts of alginic acid. Such alginates are available under the trade name PRONOVA. For aseptic coating without terminal sterilization, sterile sodium alginate is preferred. Such low endotoxin alginates are preferred especially if such reduced endotoxin content alginates satisfy regulatory requirements for endotoxin content. By reduced endotoxin it is meant that the endotoxin content of the alginate used to prepare the coating and the endotoxin content of the medical device together must not exceed, for example, the U.S. Food and Drug Administration recommended endotoxin content of an implantable medical device. The current regulatory guidelines establish that a device may not release to the patient more than 350 EU (5 EU/kg).

Chitosan is a linear polysaccharide that is composed of randomly distributed D-glucosamine (D-units) and N-acetyl glucosamine (A-units) linked in a β(1→4) manner. The ratio between glucosamine and N-acetyl glucosamine is referred to as the degree of deacetylation. The deacetylated monomers (glucosamine) are randomly distributed along the polymer chain. Chitosan has a primary amino group that can be protonized, thereby forming a cationic biopolymer. In solution, chitosan salts will carry a positive charge through protonization of the free amino group on glucosamine. Reactivity with negatively charged surfaces is a direct function of the positive charge density of chitosan. The cationic nature of chitosan gives this polymer a bioadhesive property.

Chitosan can be degraded by the enzyme lysozyme. Lysozyme is found in mammalians in saliva, tears, blood serum and in interstitial fluid. The degradation products of chitosan are glucosamine and N-acetylglucosamine. These degradation products are non-toxic in mammals.

Chitosans suited for use in the present invention are non-crosslinked water soluble salts of chitosan and preferably include reduced endotoxin, well-characterized chitosan preparations. Such chitosans are available under the trade name PROTASAN. Reduced endotoxin means that the endotoxin content of the chitosan coating and the endotoxin content of the medical device together should not exceed the recommended endotoxin limits for implantable medical devices.

Hyaluronate is a linear polymer that is composed of glucuronic acid and N-acetylglucosamine monomerslinked alternately by β(1→3) and β(1→4) glycosidic bonds. Hyaluronate is a major component of the extracellular matrix of human skin, joints, and most organs and tissues. Solutions of hyaluronan can be very viscous and are lubricious. On wetting a film comprised of hyaluronate, the coating becomes very slippery, and will dissolve over time as long as hyaluronate is not cross-linked.

Hyaluronate is degraded by the enzyme hyaluronidase. In mammals hyaluronan has an very high rate of turnover. The half-life of hyaluronan in the bloodstream of mammals is about 5 minutes. Hyaluronidase is found in tissues and cells, blood plasma, synovial fluid, and urine.

The salts of hyaluronic acid to be used in the present invention are non-crosslinked water soluble salts thereof.

Preferred salts of alginic acid, hyaluronic acid and chitosan have an endotoxin content of less than 100 endotoxin units per gram.

The coated medical device to be coated within the scope of this invention include all devices, instruments, structures, etc. intended to be in contact with at least one mammalian body fluid. The devices can be prepared by coating the exposed surface in part or completely with the soluble biopolymer coating solution of the present invention. For example, this can be done by submersing the device into the biopolymer coating solution of the present invention and then allowing excess solution to drain from the device. Alternately, the coating may be applied by spraying techniques, dipping techniques and other techniques that allow the biopolymer coating solution to come into contact with the device or device surface. The coating is then dried in an appropriate atmosphere (low humidity, temperature-controlled, dust-free, and sterile if aseptic processing is required).

Examples of medical devices that can be coated using biopolymer solutions are: plastic and metal tubing(s), plastic and metal catheters, plastic and metal cannulas and needles or needle-assemblies, surgical instruments such as clamps, forceps, retractors, etc., sutures, plastic (such as polyethylene) strips, meshes, and slings. The utility of the present invention extends to other devices not specifically listed here that may be partially or fully coated using the formulations suggested. Optional surface treatment of the medical device can be performed prior to coating to promote attachment of the biopolymer coating.

It is desirable in the present invention that at least the exposed surface coating layer does not remain with the device but rapidly dissolves away from the device. This layer may be removed prior to use, for example, to maintain sterility of surgical instrument or after placement, for example, to allow suturing prior to dissolution from a coated medical device. This layer may also be activated prior to use, for example, to obtain properties such as adhesiveness or lubricity. In the present invention, the dissolvable biopolymer coating compositions generally do not use cross-linking components (as such generally undesirably slow the dissolution of the coating) and, therefore, dissolve away from the coated device within minutes. The rate of dissolution may be controlled by adjusting the biopolymer composition. The rate of dissolution of the coating composition can be moderated by choice of the biopolymer used and in the design of the coating. For example, high viscosity, high molecular weight biopolymer would hydrate and dissolve slower than a low viscosity, low molecular weight biopolymer. In one embodiment of the present invention, both low viscosity and medium viscosity sodium alginates are combined. The purpose of this is to allow the low viscosity sodium alginate to dissolve first while the rate of dissolution is longer from the medium viscosity sodium alginate. Alternatively, coating a medical device using successive coatings, i.e. an inner coating with one biopolymer coating of the invention having a certain viscosity/molecular weight followed by an outer coating with another biopolymer coating having different viscosity/molecular weight can affect the dissolution characteristics of the coating.

The volumes and concentrations of the biopolymers may be varied to suit the coating conditions and device to be coated. The final biopolymer concentration, as well as use of single or mixed biopolymers may be adjusted to suit the desired properties of the coating such as dissolvability of the biopolymer in body fluids, flexibility of the coating, coatability of the substrate (based on surface properties of the medical device, instrument or biocompatible structure, desired thickness, etc) and biocompatibility of the biopolymer with the host to which the coated medical device is used or implanted. For coatings of implantable devices, ultrapurified biopolymers should be chosen due to their reduced level of endotoxins. Additional properties which are desirable include stability of the biopolymer coating over long periods of time prior to use (increased shelf life) and attachment of the coating to the medical device or its surface until removed by dissolution, preferably without the requirement for chemical reactivity. For the avoidance of doubt, unless expressly set forth otherwise, all wt % set forth herein for the components in the coating on the device are wt % based on the coating at the time of application to the device.

Other ingredients may be included such as antibiotic agents, e.g., gentamicin, vancomycin and other antibiotic preparations. Additional viscosity inducing agents may be added such as carboxymethyl cellulose or other cellulosic derivatives known to one skilled in the art and/or polyvinyl alcohol. Anesthetic agents may also be included in the formulation, such a lidocaine or other agents known to one skilled in the art. A monovalent, antibiotic cation such as silver may also be included.

A plasticizer may also be included to provide flexibility where desired. Such plasticizers may be chosen from glycerol, sorbitol, polyethylene glycol and other materials known to one skilled in the art. The plasticizer can be present at up to 20% of the solution. Plasticizers may be used if the coating is too brittle. Such brittleness, if too extreme, can lead to undesirable breakage, splitting, fracturing, flaking or otherwise crumbling of the coating. On the other hand, higher amounts of plasticizer in some situations may lead to an increase in the tackiness of the coating beyond that which is desired. Plasticizers should preferentially be uncharged, water-soluble and biocompatible. The chosen plasticizer should not interact with the biopolymers of the invention in such a manner that would cause precipitation of the biopolymer, reduced flexibility of the coating, or induce any other detrimental effect.

Additionally, the concentration and type of the plasticizer may be varied. In the following examples glycerol to a final concentration of 10% in the coating was used when applied to the device. However, this concentration may be varied to suit the properties of the final coating (dried), in some instances reduced glycerol concentrations may be used.

The method of drying the biopolymer coating onto the device can be either air drying in a dust-free environment, or accelerated drying using a drying oven. However, due to the nature of the biopolymer, drying conditions should not exceed 40 to 80° C. Higher temperatures can lead to a decomposition of the biopolymer that in turn can affect the ability of the biopolymer coating to hydrate and dissolve.

In order to be used for biomedical purposes, such coated medical devices must be terminally sterilized. There are several methods of sterilization, the selected manner of sterilization must be appropriate to ensure integrity of the medical device. In order to ensure utility of the biopolymer coating, sterilization using ethylene oxide is preferred to standard autoclaving. E-beam sterilization is preferred to gamma-irradiation techniques. Preferred methods of sterilization lead to less degradation of the biopolymer coating than other sterilization techniques. Sterilization using aqueous alcohol prior to packaging should be avoided as the water content in the alcohol will initiate hydration and dissolution of the coating.

Packaging should be designed to allow the coated medical device to remain sterile and free from contamination during the shelf life of the product. In addition, the packaging should prevent the ingress of humidity that could be detrimental to the coating.

The device of the present invention may have the device partially or fully embedded within the coating of the invention.

The following methods were used in the preparation of the examples:

Viscosity: Apparent viscosity was determined at 20° C. using a Brookfield rotational viscometer and a Small Sample Adapter using spindle number 21, or an UL-adapter using spindle number 00. For all biopolymers, except Protanal LFR 5/60, viscosity was assayed in a 1% (w/w) aqueous solution wherein the weight was corrected for the dry matter content. Viscosity of Protanal LFR 5/60 was assayed in a 10% aqueous solution.

Endotoxin content: The kinetic limulus amebocyte lysate (LAL) assay was used to determine the endotoxin content. The Kinetic QCL LAL kit from BioWhittaker was used, although other commercial providers may be used.

Content of guluronate and mannuronate: The G and M content of alginates was determined by using proton nuclear magnetic resonance (NMR) spectroscopy. The method used is compliant with ASTM F 2259 standard test method.

The following procedure was used for preparation of coated polyethylene mesh strip except as otherwise noted. The mesh strip was attached to a glass surface by use of adhesive tape at each end of the strip. The mesh strip was extended, but not stretched, onto the glass surface and then attached. The biopolymer mixture was poured onto the strip to coat the mesh and to cover the sides of the strip. The solution viscosity was sufficient to retain the coating on the mesh strip. The coated mesh strip was then air dried overnight. If desirable the coating process can be repeated, which was the case in Examples 1 through 7 described below. The dried biopolymer coated polyethylene mesh strip was removed from the glass surface.

The present invention will now be further described with reference to specific examples. It should be understood that these examples are intended to be illustrative only, and the present invention is not limited to the conditions, materials or devices recited in these examples. In this specification, all parts and percentages are by weight unless otherwise noted.

EXAMPLES

Example 1

The following aqueous low endotoxin alginate formulations were prepared:

(A) An aqueous alginate formulation was prepared with 10% (v/v) of glycerol and 5% of a guluronate-rich sodium alginate. 25 grams of PRONOVA UP LVG sodium alginate (175 mPas (1% solution), <700 EU/gram endotoxin content) was dissolved in 425 ml de-ionized water containing 50 ml of glycerol.

(B) An aqueous alginate formulation was prepared with 10% (v/v) of glycerol and 5% of guluronate-rich sodium alginate using a blend of differing molecular weights. 15 grams of PRONOVA UP LVG sodium alginate (79 mPas (1% solution), 69% guluronic acid, <100 EU/gram endotoxin content) and 10 grams of PRONOVA UP MVG sodium alginate (385 mPas (1% solution), <500 EU/gram endotoxin content) were dissolved in 425 ml of de-ionized water with 50 ml of glycerol added.

(C) An aqueous alginate formulation was prepared with 10% (v/v) glycerol and 5% of a mannuronate-rich sodium alginate of medium to lower viscosity. 25 grams of PRONOVA LVM sodium alginate (135 mPas (1% solution)) was dissolved in 425 ml de-ionized water containing 50 ml of glycerol.

(D) An aqueous alginate formulation was prepared with 10% (v/v) glycerol and 5% of a mannuronate-rich sodium alginate using a blend of differing molecular weights.

15 grams of PRONOVA UP LVM (58% mannuronic acid, 27 mPas (1% solution), 130 EU/gram endotoxin content) and 10 grams of PRONOVA MVM (200 mPas) were dissolved in 425 ml of de-ionized water with 50 ml of glycerol added.

(E) An aqueous alginate formulation was prepared by mixing on a 1:1 volume ratio the guluronate alginate (PRONOVA UP LVG) from example 1(A) and the mannuronate alginate (PRONOVA UP LMV) from example 1(C).

(F) An aqueous alginate formulation was prepared by mixing equal volumes of a 2.5% (w/v) PRONOVA UP MVG sodium alginate (385 mPas (1% solution), 72% guluronic acid, <500 EU/gram endotoxin content) with 2.5% (w/v) PRONOVA UP MVM sodium alginate (200 mPas (1% solution), 58% mannuronic acid, <1500 EU/gram endotoxin content). The formulation also contained 10% glycerol.

Each mixture was used to coat a polyethylene mesh strip. The mesh strip was attached to a glass surface. The biopolymer mixture was poured onto the strip to coat the mesh and to cover the sides of the strip. The increased viscosity of the mixture kept the solution on the mesh strip. The coated mesh strip was then air dried overnight. If desirable the coating process can be repeated. The dried alginate-coated polyethylene mesh strip was removed from the glass surface. The coated mesh strip was flexible and could be cut without fragmentation of the coating. The coating thickness after drying was approximately 0.5 mm, whereas the mesh strip had a thickness of approximately 0.3 mm. The coated sample was placed in a beaker containing 1000 ml of a 0.9% NaCl solution at room temperature. There was gentle agitation using a magnetic stirrer and stirring bar, approximately 20 rpm. On observation, all biopolymer coatings dissolved within 30 minutes.

Example 2

A biopolymer coating can also be produced under aseptic conditions using sterile sodium alginate. In the following cases, the polyethylene mesh strip was dipped into the following alginate solutions under aseptic conditions.

(A) A 4% (w/v) solution of sterile sodium alginate was made up by dissolving 0.25 g PRONOVA SLG 100 (147 mPas (1% solution), 67% guluronic acid, <25 EU/gram endotoxin content) in 5.6 ml of sterile de-ionized water together with 0.62 ml of sterile glycerol.

(B) A 4% (w/v) solution of sterile sodium alginate was made up by dissolving 0.25 g PRONOVA SLM 100 (230 mPas (1% solution), 57% mannuronic acid, <25 EU/gram endotoxin content) in 5.6 ml of sterile de-ionized water together with 0.62 ml of sterile glycerol.

The resulting solutions were used to coat a sterile polyethylene mesh strip by immersing the strip into the alginate solution using aseptic techniques. Excess solution was allowed to run off of the mesh strip that was then placed onto a glass surface. The mesh strip was air-dried in a laminar air-flow hood overnight. By differential weighing it was determined that there was 0.03 grams of alginate per centimeter of polyethylene mesh. The coated mesh strip was flexible and could be cut without fragmentation of the coating.

Example 3

An aqueous coating formulation was prepared containing 4% (w/w) chitosan chloride (PROTASAN UP CL 214, 81 mPas (1% solution), 95% deacetylated, <520 EU/gram endotoxin content) and 10% glycerol. 1.0 g of this solution was used to coat 5 cm$^2$ (5 cm by 1 cm) of a mesh strip as described in Example 1. The coated mesh strip was then air dried overnight in room temperature. The coated mesh strip was flexible and could be cut without fragmentation of the coating.

2.5 cm of the coated sample was placed in a beaker containing 25 ml room tempered simulated gastric fluid without enzyme. There was gentle agitation using a magnetic stirrer and stirring bar, approximately 20 rpm. On observation, all chitosan coating was dissolved within 30 minutes. The simulated gastric acid was made according to US Pharmacopeia; 2.0 g sodium chloride, 7 ml hydrochloric acid and MilliQ-water (MQ-water) to a total volume of 1000 ml.

Example 4

An aqueous solution was prepared containing 2.5% (w/w) sodium hyaluronate (HA) (SODIUM HYALURONATE PHARMA GRADE 80, $M_w$: $1.08*10^3$ kDa, <0.8 EU/gram endotoxin content) and 10% glycerol. 1.0 g of this solution was used to coat 5 cm$^2$ of a mesh strip as described in Example 1. The coated mesh strip was then air dried overnight in room temperature. The coated mesh strip was flexible and could be cut without fragmentation of the coating.

5 cm of the coated sample was placed in a beaker containing 50 ml room tempered model physiological solution (Hanks' balanced salt solution, H8264, Sigma-Aldrich Chemie GmbH, Steinheim, Germany). Small volumes were pipetted out of the solution during stirring for quantification of dissolved hyaluronate as a function of time. The assay was performed based on the method for quantitative determination of uronic acids described by Filisetti-Cozzi, T. M. C. C. and Carpita, N. C. (*Anal. Biochem.*, 197, 157-162 (1991)). A standard curve was made from three reference solutions (100-, 150-, and 200 µg/ml) of the same HA as used in the coating. The equation used for calculations was obtained from the absorbance values at 520 nm for the reference solutions listed above and a blank (correlation coefficient: $R^2$=0.99). Table 1 presents the calculated amount of dissolved HA±1 SD as a function of time, relatively to total amount of HA in coating.

TABLE 1

Dissolution rate of coating made from HA in model physiological solution.

| Time, [min] | Recovered HA ± 1 SD, [%] |
|---|---|
| 5 | 12 ± 1 |
| 10 | 16 ± 0 |
| 15 | 25 ± 9 |
| 20 | 33 ± 6 |
| 30 | 47 ± 15 |
| 45 | 84 ± 1 |
| 60 | 102 ± 4 |
| 75 | 102 ± 3 |

The results show 100% recovery of the HA used to prepare the coating within 60 minutes.

Example 5

An aqueous solution was prepared with 5% (w/w) of a mannuronate rich sodium alginate (PROVONA UP LVM, 135 mPas (1% solution) the same as used in Example 1 sample (C)) and 10% glycerol. 1.0 g of this solution was used to coat 5 cm$^2$ of a mesh strip as described in Example 1. The coated mesh strip was then air dried overnight in room temperature. The coated mesh strip was flexible and could be cut without fragmentation of the coating.

The rate of dissolution was determined as described in Example 4. A standard curve was made from five reference solutions (50-, 75-, 100-, 150-, and 200 µg/ml) of the same alginate as used in the coating. The equation used for calculations was obtained from absorbance values at 520 nm for the reference solutions listed above (correlation coefficient:

$R^2$=0.99). Table 2 presents the calculated amount of dissolved alginate±1 SD as a function of time, relatively to total amount of alginate in coating.

TABLE 2

Dissolution rate of coating made from alginate in model physiological solution.

| Time, [min] | Recovered alginate ± 1 SD, [%] |
|---|---|
| 5 | 14 ± 0 |
| 10 | 33 ± 0 |
| 15 | 53 ± 1 |
| 20 | 77 ± 2 |
| 30 | 103 ± 0 |
| 45 | 103 ± 2 |
| 60 | 102 ± 5 |

The results show 100% recovery of the alginate used to prepare the coating within 30 minutes.

Example 6

An aqueous solution was prepared containing 1.25% (w/w) HA, 2.5% (w/w) alginate and 10% glycerol. The HA and alginate used are the same as presented in Examples 4 and 5 respectively. 1.0 g of this solution was used to coat 5 cm of a mesh strip as described in Example 1. The coated mesh strip was then air dried overnight in room temperature. The coated mesh strip was flexible and could be cut without fragmentation of the coating.

2.5 cm of the coated sample was placed in a beaker containing 25 ml room tempered Hanks' solution. There was gentle agitation using a magnetic stirrer and stirring bar, approximately 20 rpm. On observation, all coating was dissolved within 60 minutes.

Example 7

The following aqueous alginate formulations were prepared:

(A) An aqueous alginate formulation was prepared with 10% (v/v) of glycerol and 5% of a guluronate-rich sodium alginate. 25 grams of PRONOVA UP LVG sodium alginate (79 mPas (1% solution), 69% guluronic acid, <100 EU/gram endotoxin content) was dissolved in 425 ml de-ionized water containing 50 ml of glycerol.

(B) An aqueous alginate formulation was prepared with 10% (v/v) of glycerol and 5% of a mannuronate-rich sodium alginate. 25 grams of PRONOVA LVM sodium alginate (135 mPas (1% solution)), was dissolved in 425 ml de-ionized water containing 50 ml of glycerol.

Each mixture was used to coat polyethylene mesh strips as explained in Example 1. Alginate coated polyethylene mesh strips were gamma-irradiated with a dose of 29.5 kGy. Control samples not subjected to gamma-irradiation were kept. Gamma-irradiated samples of coated polyethylene mesh had the same flexibility as control samples not irradiated. The films of irradiated samples were transparent with a gleam of yellow, while films of control samples (not irradiated) were transparent.

Film coatings were dissolved by placing a 0.5 cm piece of coated mesh in a sodium sulphate buffer. Resulting solutions were directly used to measure molecular weight using Size Exclusion Chromatography with laser Light Scattering (SEC-MALS). Weight average molecular weight (Mw) of alginate in coatings from control samples (not irradiated) were 120 000 g/mol and 150 000 g/mol for formulations (A) and (B) respectively, while Mw of alginate in gamma-irradiated samples were 50 000 and 60 000 g/mol for formulations (A) and (B) respectively.

The invention has been illustrated by detailed description and examples of the preferred embodiments. Various changes in form and detail will be within the skill of persons skilled in the art. Therefore, the invention must be measured by the claims and not by the description of the examples or the preferred embodiments.

What is claimed is:

1. A medical device comprising a biocompatible medical coating adhered thereto, wherein said biocompatible medical coating consists of one or more layers each comprising at least one water soluble salt of: (i) alginic acid, (ii) hyaluronic acid or (iii) chitosan; wherein (a) said coating is fully dissolved in interstitial fluid in less than 1.0 hour; (b) said water soluble salt has an endotoxin content of <100 endotoxin units/gram; (c) said medical device comprises plastic and metal tubing; plastic and metal catheters; plastic and metal cannulas, needles and needle assemblies; and surgical instruments; and (d) said water soluble salt consists of at least one non-crosslinked, water soluble salt of alginic acid, hyaluronic acid or chitosan.

2. A device of claim 1 wherein said coating further comprises a plasticizer.

3. A device of claim 1 wherein said water soluble salt comprises a mixture of:
(i) a low viscosity sodium alginate and (ii) a medium or high viscosity sodium alginate.

4. A device as claimed in claim 3 wherein the low viscosity sodium alginate has a viscosity in a 1% solution measured at 20° C. of 2 to 100 mPas, and the medium or high viscosity sodium alginate has a viscosity of 100 to 500 mPas in a 1% solution measured at 20° C.

5. A device as in claim 3 comprising 0.5 to 20% of a plasticizer.

6. A device of claim 1, wherein said salt of alginic acid comprises at least one of sodium alginate, potassium alginate or magnesium alginate.

7. A device as in claim 1 wherein said salt of chitosan comprises chitosan chloride.

8. A device as in claim 7 wherein the concentration of chitosan chloride is 0.5 to 10% by weight of the total composition.

9. A device as in claim 1 wherein said salt of chitosan comprises chitosan glutamate.

10. A device as in claim 9 wherein the concentration of chitosan glutamate is 0.5 to 10% by weight of the total composition.

11. A device as in claim 8 or 10 comprising 0.5 to 20% of a plasticizer.

12. A device as in claim 1 or 2 wherein said salt of hyaluronic acid comprises sodium hyaluronate.

13. A device as claimed in claim 12 wherein the concentration of sodium hyaluronate is 0.5 to 5% by weight of the total composition.

14. A device as claimed in claim 1 wherein said salt comprises a mixture of sodium alginate and chitosan.

15. A device as described in claim 1 wherein said water-soluble salt comprises a mixture of sodium alginate and sodium hyaluronate.

16. A device as in claim 1, wherein said salt of chitosan comprises chitosan acetate.

17. A device of claim 1, wherein said coating is fully dissolved in interstitial fluid in less than 50 minutes.

18. A device of claim 1, wherein said coating is fully dissolved in interstitial fluid in less than 40 minutes.

19. A device of claim 1, wherein said coating is fully dissolved in interstitial fluid in less than 30 minutes.

20. A device of claim 1 wherein said device is embedded within the coating.

21. A device of claim 1, wherein said coating is sterilizable by gamma-irridation, E-beam or ethylene oxide.

22. A device of claim 1, wherein said coating comprises at least one pharmaceutical active ingredient that is capable of being delivered locally at a site of implantation in a mammal.

23. A device of claim 1, wherein said device is a surgical instrument and said surgical instrument is a clamp, forcep, retractor, suture, plastic strip, mesh, or sling.

24. The device of claim 1, wherein said water soluble salt of alginic acid is sodium alginate and said sodium alginate is present in an amount of 1 to 10% by weight of the total coating.

25. The device of claim 1, wherein the device is a mesh.

26. The device of claim 1, wherein the device is a sling.

* * * * *